United States Patent [19]

Sugisawa et al.

[11] Patent Number: 4,559,963
[45] Date of Patent: Dec. 24, 1985

[54] SYSTEM FOR FEEDING LIQUID SUBSTANCES

[75] Inventors: Ko Sugisawa; Kazuya Sekiguchi; Masao Taguchi; Masayuki Nakatani; Hitoshi Iwata, all of Higashiosaka, Japan

[73] Assignee: House Food Industrial Company Limited, Osaka, Japan

[21] Appl. No.: 605,878

[22] Filed: May 1, 1984

[30] Foreign Application Priority Data

May 2, 1983 [JP] Japan .................... 58-78756

[51] Int. Cl.⁴ .............................. E03B 5/00
[52] U.S. Cl. ...................... 137/1; 137/567; 137/568
[58] Field of Search ............. 137/566, 567, 568, 1

[56] References Cited

U.S. PATENT DOCUMENTS

| | | | |
|---|---|---|---|
| 3,357,359 | 12/1967 | Schaub | 137/567 |
| 3,504,686 | 4/1970 | Cooper et al. | 137/568 |
| 3,754,735 | 8/1973 | Hoyle et al. | 137/566 |
| 3,763,887 | 10/1973 | MacVey et al. | 137/566 |
| 4,269,352 | 5/1981 | Przystawik | 137/566 |

FOREIGN PATENT DOCUMENTS 2812264 10/1979 Fed. Rep. of Germany ...... 137/567

Primary Examiner—A. Michael Chambers
Attorney, Agent, or Firm—Weiss & Holloway

[57] ABSTRACT

Two or more sets of liquid substance feed means are provided each which consists of a supply device, a transport pipe and a delivery pump. These feed means are connected through a valve to a single transport pipe and back pressure devices are provided in all but one of the liquid-substance feed means. While a liquid substance is being fed by one of the feeding means, another liquid substance having different properties is passing in the other feed means and using the back pressure device provided in the latter means, the flow rate and the pressure of the latter liquid substance are controlled as the same as those of the former being fed by the former feed means. Being switched over, in this condition, from the former feed means to the latter to feed the latter liquid substance, two or more kinds of liquid substance having different properties can be fed sequentially at predetermined pressure and flow rate.

3 Claims, 4 Drawing Figures

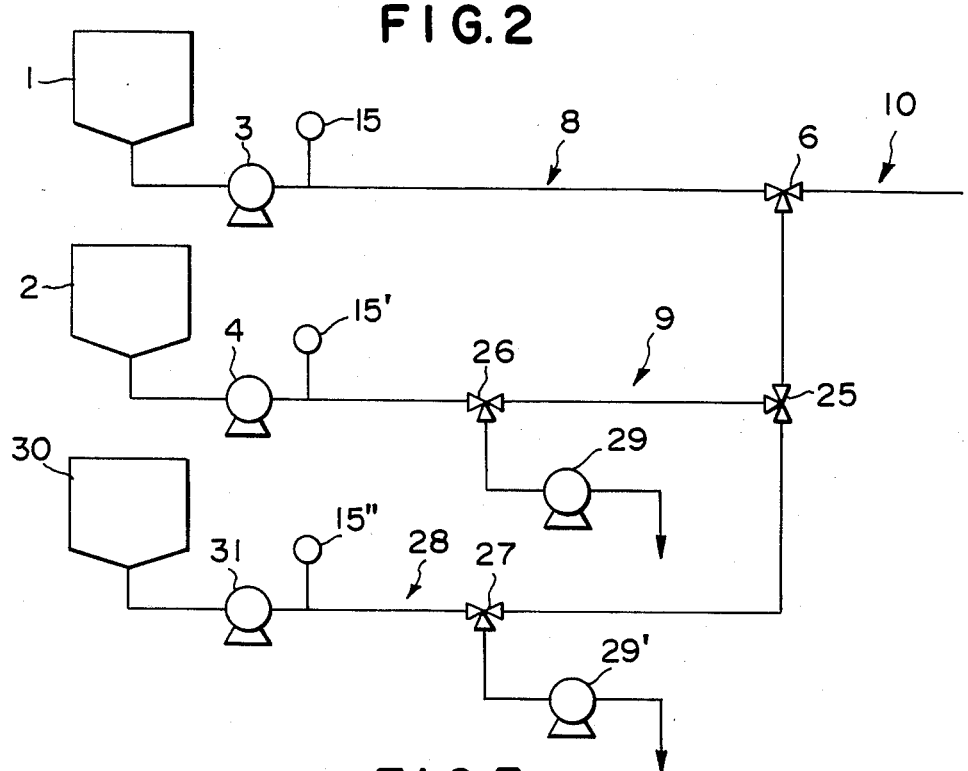
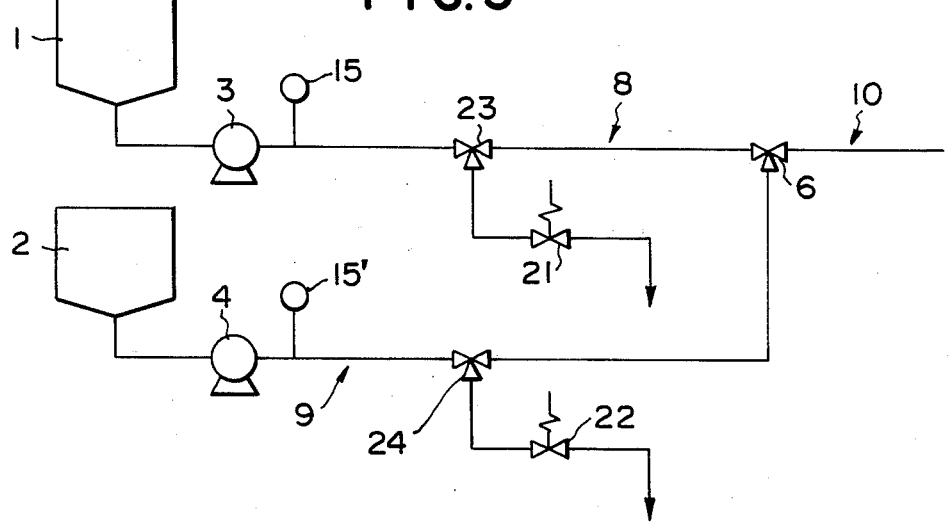

SYSTEM FOR FEEDING LIQUID SUBSTANCES

BACKGROUND OF THE INVENTION

1. Field of the Invention

The present invention relates to a system for sequentially feeding different kinds of liquid substances in such a manner that after the feeding of a given kind of liquid substance has been completed, the system is switched over to feed the next kind of liquid substance. More particularly, the present invention pertains to such a system capable of sequentially feeding two or more kinds of liquid substances having different properties without causing any changes in flow rate and pressure of the liquid substance being fed even when the system is switched over to feed the different kinds of liquid substances.

2. Description of the Prior Art

In general, when two or more kinds of liquid substances having different properties are sequentially fed, they are changed over from a given kind to the next kind of liquid substance before the latter is introduced into supply means to feed the liquid substance from the supply means into a system by means of a delivery pump. Alternatively, a plurality of supply means are provided upstream of a delivery pump, and a valve or the like provided between the supply means and the delivery pump is operated to change over the liquid substances from their one kind to the next kind. In such a method, however, when a changeover to the second liquid substance is made, the second liquid substance passes through the same delivery pump as that for the liquid substance fed before the changeover. For this reason, particularly when the changeover is effected between liquid substances having different properties, e.g., from one with a low viscosity to another with a high viscosity, from one including solid matter to another not including such matter, and vice versa, the resistance to passage of the liquid substance through the pump may vary, or there may be a change in the slip amount of the liquid substance between the rotor and stator of the pump, or the pump may be clogged with the solid matter at the clearance therein, resulting in undesirably large changes in flow rate and pressure of the liquid substance being fed after changeover.

The above problems are often encountered, particularly when it is necessary to apply a high pressure into the system. Moreover, it is extremely difficult in any attempt to prevent the occurrence of the above-mentioned problems and to adjust the delivery rate and pressure of the pump within a very short period of time and with a high accuracy when the liquid substances are changed over, due to the limited ability of the delivery pump and a lag time from when the changes in the delivery rate and pressure of the pump are detected to the time when a proper control thereof is effected.

Further, in the case where a liquid food or pharmaceutical is to be sterilized to a sufficient extent that it is microbiologically safe, that is, where a liquid substance is to be fed into a sterilizer at a predetermined flow rate and pressured and processed in the sterilizer at a constant residence time and temperature of the liquid substance, the above-mentioned problems may result in such disadvantages as sterilization failure due to insufficient heating of the liquid substance or deterioration in quality due to overheating thereof. Further, particularly, in the case where a liquid substance is processed by an aseptic processing system, there may be an occurrence of the intrusion (contamination) of germs into a sterile zone on the downstream side of the sterilizer, resulting in a fairly serious problem.

SUMMARY OF THE INVENTION

An object of the present invention is to provide a system for feeding liquid substances which is free from the above-mentioned problems.

Accordingly, it is a primary object of the present invention to provide such a system capable of sequentially feeding two or more kinds of liquid substances having different properties without causing any changes in flow rate and pressure of the liquid substance being fed after changeover.

It is another object of the present invention to provide a system for feeding liquid substances which is particularly suitable for use in an aseptic processing system.

To these ends, the system for feeding liquid substances according to the present invention comprises two or more transport pipes connected through a valve to a single transport pipe, and delivery pumps provided in the respective transport pipes upstream of the junction. Further, there is provided a back pressure device adapted to discharge a liquid substance while maintaining it at a predetermined pressure, and it is provided in all but one of the transport pipes between the valve and the delivery pump. In operation: (1) a given kind of liquid substances is passed through one of the transport pipes upstream of the junction and is fed by the delivery pump provided therein; (2) in the meantime, a liquid substance having different properties from that in (1) is passed through another transport pipe upstream of the junction and is discharged outside the system by the other delivery pump and back pressure device at the flow rate and pressure which are equal to those of the liquid substance in (1); and (3) the valve provided at the junction of the transport pipes is actuated to change over from the liquid substance in (1) to that in (2). In this case, the delivery pumps and the back pressure devices serve to uniformly maintain the flow rate and pressure of each of the liquid substances in the transport pipes upstream of the junction. Therefore, the changing over of liquid substances having different properties in the respective transport pipes from one to the other is very smoothly and continuously effected and there are no changes in flow rate and pressure of the liquid substance being fed after the changeover.

Accordingly, the objects of the present invention are accomplished by providing a system for feeding liquid substances which is capable of sequentially feeding two or more kinds of liquid substances having different properties at a predetermined pressure and flow rate, the system comprising at least two liquid-substance feed means each including a supply device, transport pipe in communication with the supply device and a delivery pump provided in the transport pipe; a single transport pipe connected through a valve to said transport pipes; and back pressure device provided in one of the liquid-substance feed means intermediate the delivery pumps and the valve and adapted to discharge a liquid substance while maintaining it at a predetermined pressure

BRIEF DESCRIPTION OF THE DRAWINGS

The invention will be described hereinunder in detail with reference to the accompanying drawings wherein:

FIGS. 1 to 3 are flow charts showing embodiments of the liquid-substance feed system in accordance with the invention.

DESCRIPTION OF THE PREFERRED EMBODIMENTS

Figure 1:
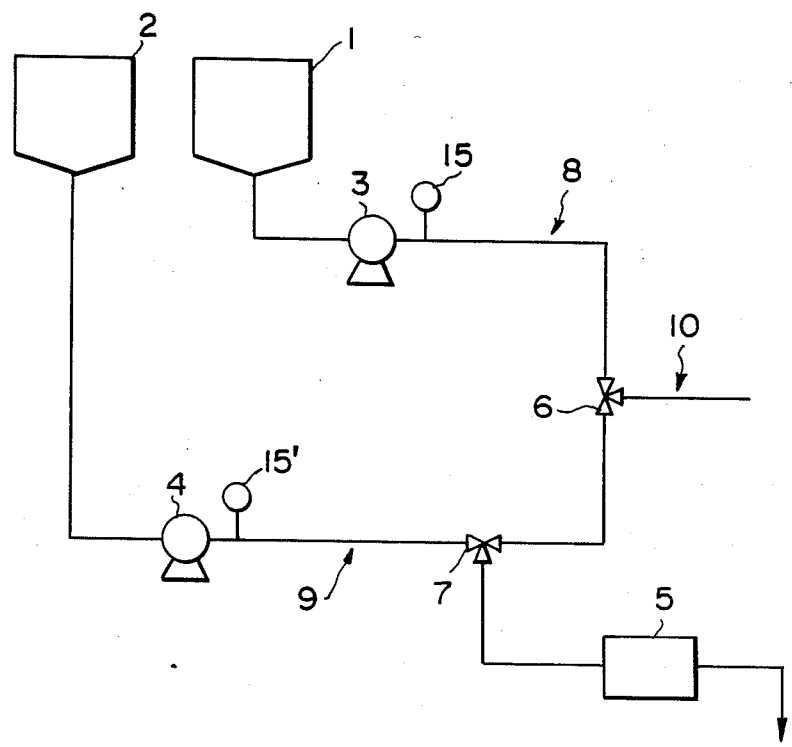

FIG. 1 is a flow chart showing a preferred embodiment of the invention in which the system comprises a transport pipe 8 provided with a product tank 1 and a delivery pump 3, and a transport pipe 9 provided with a product tank 2 and a delivery pump 4 and a single transport pipe 10 connected through a three-way valve 6 to the pipes 8 and 9. A back pressure device 5 is provided in piping which is connected through a three-way valve 7 to a part of the transport pipe 9 intermediate the delivery pump 4 and the three-way valve 6.

When this system is actually operated, first, a liquid substance is supplied from its supply means, e.g., the product tank 1 into the transport pipe 8 and is then fed through it to the transport pipe 10 by the delivery pump 3. In this case, as the delivery pump 3, it is preferable to employ a pump such as a piston pump, snake pump or rotary pump which is relatively high in quantitative properties. These pumps may be combined with another pump, e.g., a centrifugal pump, which is large in flow rate, and is provided in the transport pipe 8.

It is to be noted that in the above arrangement the three-way valve 6 is in a state where the transport pipes 8, 9, 10 are in communication with each other, or in a state where the transport pipes 8 and 10 are in communication with each other but the valve 6 cuts off the communication between the transport pipes 8 and 10, on one hand, and the transport pipe 9 on the other. However, when the three branches of the valve 6 are all opened, it is necessary to change over the three-way valve 7 so as to permit the communication between the part of the transport pipe 9 upstream of the three-way valve 7 and the piping connected with the back pressures device 5 but to cut off the communication between the parts of the transport pipe 9 upstream and downstream of the three-way valve 7.

Under this condition, while the liquid substance is being fed from the product tank 1 through the pipe 8 to the transport pipe 10, a liquid substance having different properties from the above liquid substance is supplied from the product tank 2 into the transport pipe 9 and is discharged outside the system through the delivery pump 4 and the back pressure device 5. In this case, the delivery pump 4 has quantitative properties similarly to the above-mentioned delivery pump and may be provided in the transport pipe 9 in combination with another pump. The back pressure device 5, on the other hand, serves to discharge the liquid substance while maintaining a predetermined pressure in the part of the system upstream of the back pressure device 5. As the back pressure device 5, it is possible to employ, e.g., a pressure control valve (safety valve), a pump with a small leak, and a tank capable of controlling the air pressure. It is to be noted that when the liquid substance to be fed includes solid matter or has a high viscosity, it is particularly effective to employ a tank capable of controlling the air pressure of a rotary pump with a slight leak.

The operation of the system will be described hereinunder in further detail. While the liquid substance is being fed from the product tank 1 through the pipe 8 into the transport pipe 10 by the delivery pump 3, the threeway valve 7 is in such a state as to permit the communication between the part of the transport pipe 9 upstream the three-way valve 7 and the piping connecting with the back pressure device 5 but to cut off the communication between the part of the transport pipe 9 upstream of the three-way valve 7 and the piping connecting with the back pressure device 5, on one hand and the part of the transport pipe 9 downstream the three-way valve 7 on the other. Accordingly, the liquid substance is supplied from the tank 2 through the pipe 9 to the back pressure device 5 by the delivery pump 4. In this case, the pressure in the part of the system upstream the back pressure device 5 is controlled by the back pressure device 5 so as to be equal to the pressure in the part of the transport pipe 8 downstream the delivery pump 3 (the pressure measured by a pressure gauge 15).

At the same time, the number of revolutions of the delivery pump 4 is adjusted so that the flow rate of the liquid substance discharged through the back pressure device 5 is equal to that of the liquid substance in the part of the transport pipe 8 downstream the delivery pump 3. By these controlling operations, the flow rate and pressure of the liquid substance having passed through the discharge pump 4 becomes equal to those of the liquid substance having passed through the delivery pump 3. It is to be noted that in the above operation the liquid substance discharged outside the system after passing through the back pressure device 5 can, needless to say, be collected into the product tank 2 again so as to be recirculated.

After a predetermined amount of the liquid substance has been supplied from the product tank 1 into the transport pipe 10 or the supply of the liquid substance has been effected for a predetermined period of time, the three-way valve 6 is actuated so as to cut off the communication between the transport pipes 8 and 10 but to allow the communication between the transport pipes 9 and 10. At the same time, the three-way valve 7 is actuated so as to cut off the communication between the part of the transport pipe 9 upstream the three-way valve 7 and the piping connecting with the back pressure device 5 but to permit the communication between the parts of the transport pipe 9 upstream and downstream the three-way valve 7. The above operations cause the liquid substance to be fed to the transport pipe 10, to be instantaneously changed over from that supplied from the product tank 1 to that supplied from the product tank 2. In this case, as described above, the flow rate and pressure of the liquid substance supplied from the product tank 2 and having passed through the discharge pump 4 are equal to those of the liquid substance having passed through the delivery pump 3 beforehand, regardless of any difference in properties between the liquid substances. Therefore, even if liquid substances having different properties are changed over from one to the other, there are no changes in flow rate and pressure of the liquid substance passing through the transport pipe 10 at all, and the changeover operation is very smoothly effected.

It is to be noted that although there are provided two liquid-substance feed means (the transport pipes upstream the junction each equipped with the liquid substance supply means and the delivery pump in FIG. 1) the number of the liquid-substance feed means is not exclusive and it is possible to provide three or more liquid-substance feed means in the system of the invention. More specifically, the provision of three liquid-substance feed means as shown in FIG. 2 makes it possible to continuously feed three kinds of liquid substances having different properties at a predetermined flow rate and pressure by supplying the liquid substances to the respective liquid-substance feed means and successively feeding the liquid substances while changing over the same from one to another.

Further, although in FIG. 1 the back pressure device 5 is provided only for the transport pipe 9, the system of the invention requires that back pressure devices be provided in all but one of the liquid-substance feed means upstream of the junction, and it is also possible to provide back pressure devices between the delivery pumps and the valve provided at the junction of the transport pipes for all the liquid-substance feed means.

FIG. 2 is a flow chart showing another embodiment of the present invention in which the system comprises a transport pipe 8 provided with a product tank 1 and delivery tanks 2, 30 and transport pipes 9, 28 provided with product tanks 2, 30, respectively, and delivery pumps 2, 30, respectively, and a single transport pipe 10 connected through three-way valves 6, 25 to the pipes 8, 9 and 28. Delivery pumps 29, 29' are provided in piping which are connected through three-way valves 26, 27, respectively, to parts of the transport pipes 2, 28, respectively, intermediate the delivery pumps 4, 31 and the three-way valves 6, 28.

FIG. 3 shows another embodiment of the invention in which back pressure devices are provided for all the liquid-substance feed means. According to this embodiment, there are provided two liquid-substance feed means equipped with respective back pressure devices in the form of pressure control valves 21 and 22 connected through three-way valves 23 and 24 to the pipes 8 and 9, respectively.

In operation:

(1) The three-way valve 6 is actuated so as to permit the communication between the transport pipes 8 and 10 but to cut off the communication between the transport pipes 9 and 10. Further, the three-way valve 23 is actuated so as to permit the communication between the parts of the transport pipe 8 upstream and downstream the three-way valve 23 but to cut off the communcation between the transport pipe 8 and a piping connecting with the pressure control valve 21. Under this condition, a liquid substance is fed from the product tank 1 to the transport pipes 8, 10 through the delivery pump 3.

(2) In the meantime, a liquid substance having different properties from that fed to the transport pipe 8 is fed to the transport pipe 9 and is discharged outside the system by the delivery pump 4 and the pressure control valve 22 so that the flow rate and pressure of the liquid substance in the transport pipe 9 are equal to those of the liquid substance in the transport pipe 8 (in this case, the three-way valve 24 provided in the transport pipe 9 is in such a state as to cut off the communication between the parts of the transport pipe 9 upstream and downstream the three-way valve 24 but to permit the communication between the part of the transport pipe 9 upstream the three-way valve 24 and the piping connecting with the pressure control valve 22).

(3) Then, the three-way valve 6 is actuated so as to cut off the communication between the transport pipes 8 and 10 but to permit the communication between the transport pipes 9 and 10. Simultaneously, the three-way valve 24 is actuated so as to cut off the communication between the parts of the transport pipe 9 upstream and downstream the three-way valve 24 and the piping connecting with the pressure control valve 22 but to permit the communciation between the parts of the transport pipe 9 upstream and downstream the three-way valve 24, thereby to effect a changeover from the liquid substance through the transport pipe 8 to the liquid substance through the transport pipe 9.

(4) While the liquid substance is being fed through the transport pipe 9, the three-way valve 23 is actuated so as to permit the communication between the part of the transport pipe 8 upstream the three-way valve 23 and the piping connecting with the pressure control valve 21. Under this condition, a new liquid substance having different properties from the liquid substances in (1) and (2) is fed into the transport pipe 8 and is discharged outside the system by the discharge pump 3 and the pressure control valve 21 so that the flow rate and pressure of the liquid substance are equal to those of the liquid substance in the transport pipe 9.

(5) Then, the three-way valve 6 is actuated so as to cut off the communication between the transport pipes 9 and 10 but to permit the communication between the transport pipes 8 and 10. Simultaneously, three-way valve 23 is actuated so as to cut off the communication between the part of the transport pipe 8 upstream the three-way valve 23 and the piping connecting with the pressure control valve 21 but to permit the communication between the parts of the transport pipe 8 upstream and downstream the three-way valve 23 to effect a changeover from the liquid substance through the transport pipe 9 to that through the transport pipe 8, thereby allowing three kinds of liquid substances having different properties to be continuously fed at a predetermined flow rate and pressure. It is to be noted that it is, needless to say, possible to feed further various kinds of liquid substances having different properties by repeating the above operations.

Moreover, although in the embodiment of FIG. 1 the valve is disposed at the junction of the transport pipes, the valve may be provided in the transport pipes at any position downstream the delivery pumps and downstream the back pressure device, if it is provided, provided that it is possible to change over liquid substances from one to another as described above. In addition, the valve is not limited to the three-way valve.

The following is the description of the system of the invention in the case where it is employed for an aseptic processing system, for example.

Figure 4:
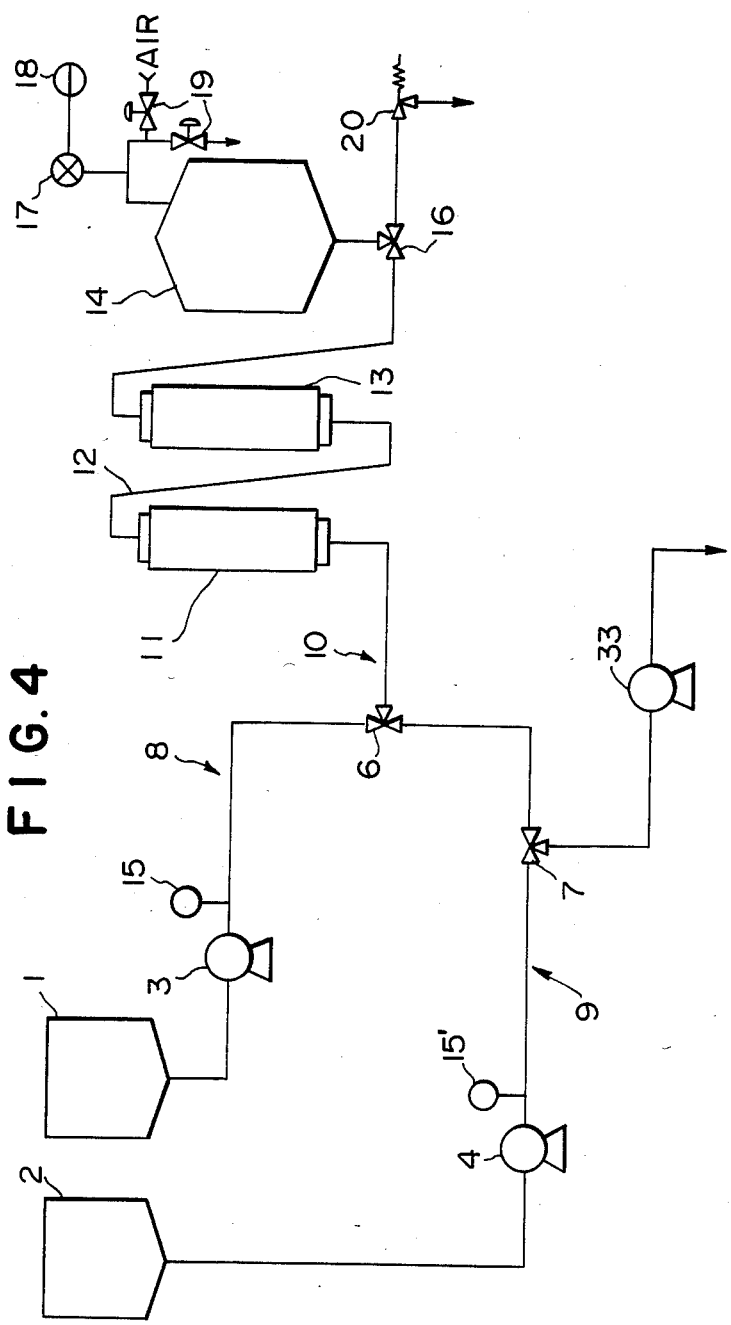
FIG. 4 is a flow chart showing an example of an aseptic processing system to which the liquid-substance feed system of the invention is applied.

In operation of an aseptic processing system, the system is generally run according to the following steps: a first step in which, before the start of an operation, the system is previously sterilized by means of hot water under a temperature of 130° to 150° C. for more than 30 minutes in order to ensure the asepsis of the whole of the system (referred to as "sterilization of the system", hereinafter); a second step in which while the system is being sterilized a cooler is operated to cool the hot water (referred to as "water operation", hereinafter); and a third step in which the water operation is switched over to an actual operation so that the water is completely replaced with a liquid substance to be actually processed (referred to as "actual liquid-substance operation", hereinafter). Referring to FIG. 4 which shows an aseptic processing system adapted for use with the liquid-substance feed system of the invention, the aseptic processing system comprises a heater 11, a holding tube 12, a cooler 13, an aseptic tank 14 and a back pressure device in the form of a pressure control valve 20 provided in the order mentioned in a piping which is connected to the transport pipe 10 of the liquid-substance feed system of the invention.

As the heater 11, it is possible to employ a heat exchanger which permits a high-temperature processing, such as a heat exchanger of plate type, tube type or surface-scraping type, or a steam injection type heater. If necessary, these devices may be employed in combination. It is to be noted that it is particularly effective to employ a surface-scraping type heat exchanger when a liquid substance to be fed include solid matter or has a high viscosity. As the cooler 13, it is possible to employ a heat exchanger or the like similar to that for the heater 11.

Moreover, the interior of the aseptic tank 14 is pressurized by introducing air under pressure thereinto. The aseptic tank 14 is provided with a pressure sensor 17 adapted to sense the pressure inside the tank 14 and a pressure controller 18 adapted to control inlet and outlet valves 19 so as to maintain the interior of the tank 14 at a predetermined pressure. In addition, the aseptic tank 14 is pressure resistant and may be provided with a stirring function if necessary.

It is to be noted that the control of the pressure inside the tank 14 which is built up by means of the air under pressure may be effected by an air regulator. If a completely aseptic produce is desired, the air to be injected into the tank 14 is required to be an aseptic air which has been passed through a germ-removing air filter, for example.

When the aseptic processing system is actually operated, in the first step of sterilizing the system, the water from the product tank 1 is fed by the delivery pump 3 through the transport pipes 8, 10 to the heater 11 where it is heated to temperatures of 130° to 150° C. The hot water heated in the heater 11 is passed through the holding tube 12 and the cooler 13 (in an inoperative state) to the pressure control valve 20 through which the water is then discharged outside the system. In this case, the pressure control valve 20 has a function similar to that of the above-described back pressure device 5. In other words, a boiling-suppressing pressure (back pressure) is applied to the inside of the system by the delivery pump 3 and the pressure control valve 20, so that the water is well heat-sterilized by the heater 11, and this hot water serves to sterilize the piping and devices through which a liquid substance to be a product passes. On the other hand, the aseptic tank 14 is separately heat-sterilized by means of steam or the like.

Moreover, upon completion of the sterilization of the system, aseptic air is introduced into the aseptic tank 14 to maintain it in an aseptic state and at a predetermined pressure under control of the pressure sensor 17, the pressure controller 18 and the control valves 19.

The water operation of the aseptic processing system is effected in the same manner as that in the case of the sterilization of the system except that the cooler 13 is operated in the water operation. Also in this operation, a back pressure is applied to the water inside the system by the pressure control valve 20.

When the sterilization and the water operation are carried out, a three-way valve 16 is switched over to permit the communication between the cooler 13 and the pressure control valve 20 and to cut off the communications between the cooler 13 and the aseptic tank 14 and between it and the pressure control valve 20.

While the sterilization of the system and the water operation are being effected, a liquid substance completely different in properties from water, e.g., a liquid substance including solid matter or having a high viscosity, is supplied by the delivery pump 4 from the product tank 2 through the transport pipe 9 and the three-way valve 7 to the back pressure device in the form of a back pressure pump 33 through which the liquid substance is discharged out of the system. In this case, by the above-described operations, the flow rate and pressure of the liquid substance having passed through the delivery pump 4 are controlled so as to be completely equal to those of the water fed through the transport pipes 8, 10 by the delivery pump 3.

Upon completion of the water operation, the three-way valves 6 and 7 are changed over to feed the liquid substance including solid matter (or having a high viscosity) through the pipes 9 and 10 to a point of the three-way valve 16 which is then actuated so as to permit the communication between the cooler 13 and the aseptic tank 14 but to cut off the communication between the cooler 13 and the aseptic tank 14 on one hand and the pressure control valve 20 on the other. By this operation, instead of the water, the liquid substance including solid matter (or having a high viscosity), from the product tank 2, is fed through the transport pipe 10 and through the heater 11, the holding tube 12 and the cooler 13 into the sterile tank 14 (actual liquid-substance operation). In this case, a back pressure is applied to the inside of the system by the discharge pump 4 and the controlled pressure in the aseptic tank 14, so that the product is prevented from boiling and is well sterilized at a sufficiently high temperature.

According to the aseptic processing system employing the liquid-substance feed system of the invention, when the water operation is switched over to the actual liquid-substance operation, the flow rate and pressure of the liquid substance fed to the heater 11 and the holding tube 13 are constant at all times, regardless of any difference in properties between the liquid substances to be fed; hence, the liquid substances are heat sterilized under the same conditions. In an aseptic processing system employing a conventional liquid-substance feed system, when the substance to be processed is changed over from water to a liquid substance having a high viscosity, for example, if the delivery pumps are equal to each other in the number of revolutions, the delivery rate of the liquid substance having a high viscosity exceeds that of the water. In consequence, the residence time of the liquid substance having a high viscosity in the sterile processing system is undesirably reduced, or the heating capacity of the heater is insufficient for maintaining a required sterilizing temperature, so that sterilization failure is apt to occur and there is a fear of intrusion of germs into the sterile zone. If the sterilizing conditions are set to be somewhat higher beforehand in the steps of sterilization of the system and the water operation in order to prevent the occurrence of the above problems, when the water operation is switched over to the actual liquid-substance operation, there may be deterioration in quality of the product due to overheating thereof. However, the employment of the liquid-substance feeding system of the invention for an aseptic processing system permits liquid substances to be sterilized under constant optimum conditions even if liquid substances having different properties are changed over from one to the other. Accordingly, it is possible to eliminate the occurrence of any bacterial contamination and maintain a proper quality of the product without producing any problems at all. In addition, the changeover operation is extremely easy and advantageous.

It is to be noted that in operation of the above-described aseptic processing system, if a liquid substance to replace the water is different in specific heat and viscosity, there may be a change in the rate of heat and viscosity, and there may be a change in the rate of transfer of heat to the liquid substance in the heater 11 after the changeover. In other words, if liquid substances to be fed are changed over from water to a liquid substance having a high viscosity, for example, there is generally a reduction in the rate of transfer of heat to the liquid substance having a high viscosity in the heater 11, so that the liquid substance after heating is apt to be lower in temperature than the water.

In such a case, the flow rate of the liquid substance having a high viscosity at which the temperature thereof after heating is coincident with a predetermined value, is experimentally obtained beforehand. While the water operation is being effected through the transport pipe 8, the flow rate of the liquid substance having a high viscosity is controlled so as to coincide with the experimentally obtained flow rate by the delivery pump 4 and the back pressure device 5 provided in the transport pipe 9, and the pressure is controlled so as to coincide with a predetermined value. Under this set of conditions, the liquid substances to be fed are changed over from one to the other (when water is replaced with a liquid substance having a high viscosity, there is generally a reduction in the heat transfer efficiency in the heater 11; therefore, the flow rate of the liquid substance having a high viscosity in the transport pipe 9 is controlled so as to be smaller than that of water). By the above operations, even if liquid substances to be fed are changed over from water to a liquid substance having a high viscosity, the high-viscosity liquid substance is sufficiently heated up so that the temperature thereof after heating is coincident with a predetermined value, and is excellently sterilized, It is to be noted that in the aseptic processing system employing the liquid-substance feeding system of the invention, the back pressure device for applying a back pressure to the inside of the system is not especially limitative and the back pressure may be applied by, for example, a pressure control valve, a pump with a small leak or a tank capable of controlling the air pressure, which is provided on the downstream side of the sterilizer in the system. If a tank capable of controlling the air pressure is employed, a back pressure can be very stably applied to the inside of the system, since the pressure control is effected through air as a medium. Also, in the case of a liquid substance including solid matter or having a high viscosity, it is possible to excellently apply a back pressure without causing any clogging or the like. Accordingly, if such tank is employed together with the liquid-substance feeding system of the invention, it becomes possible to continuously sterilize two or more kinds of liquid substances different in properties under extremely stable conditions.

As has been described, the liquid-substance feeding system of the invention makes it possible to continuously feed two or more kinds of liquid substances different in properties at a predetermined flow rate and pressure. The system of the invention is greatly useful for an aseptic processing system which sterilizes, particularly a liquid food or pharmaceutical to a sufficient extent that it is commercially aseptic.

While the invention has been particularly shown and described with reference to preferred embodiments thereof, it will be understood by those skilled in the art that the foregoing and other changes in form and details may be made therein without departing from the spirit and scope of the invention.

What we claim is:

1. A liquid substance feed system capable of sequentially feeding two or more kinds of liquid substances having different properties to a single transport pipe at a predetermined pressure and flow rate, said system comprising:

at least two liquid substance feed means each including a supply device from which a liquid substance is fed to a process apparatus, a respective transport pipe in communication with each respective supply device, and a respective delivery pump provided in said transport pipe downstream of each said supply device for the delivery of the liquid substance into a downstream transport pipe and capable of controlling the flow rate of the liquid substance;

a third transport pipe connected through a first valve to said respective pipes;

a diverged piping, provided between said delivery pumps and said first valve through another valve in one of said at least two liquid substance feed means, for discharging the liquid substance; and a back pressure device provided in said diverged piping and adapted to discharge the liquid substance while maintaining the liquid substance at a predetermined pressure.

2. A liquid substance feed system according to claim 1, wherein said system is employed for an aseptic processing system.

3. A method for feeding a liquid substance capable of sequentially feeding at least two kinds of liquid substances having different properties to a single transport pipe at a predetermined pressure and flow rate using a liquid substance feed system, said method comprising the steps of:

feeding a first liquid substance into one liquid substance feed means to pump said first liquid substance at a predetermined flow rate and pressure by a delivery pump provided in said one liquid substance feed means;

feeding another liquid substance having different properties from that of said first liquid substance into another liquid substance feed means while said first liquid substance is being pumped, and operating a valve provided between a delivery pump and a back pressure device in said another liquid substance feed means to permit said another liquid substance to flow toward the back pressure device, so that said another liquid substance flowing between the delivery pump and the back pressure device is discharged outside the system with a flow rate and pressure thereof being controlled to be equal to those of said first liquid substance which is being passed, and thereafter operating a second valve connecting both liquid substance feed means and said valve provided between said delivery pump and said back pressure in said device second liquid substance feed means in which said another liquid substance is not being passed, thereby switching over the passing from said first liquid substance which is being passed another liquid substance which has been controlled in flow rate and pressure in said another liquid substance feed means.

* * * * *